(12) United States Patent
Schneider et al.

(10) Patent No.: US 9,939,455 B2
(45) Date of Patent: Apr. 10, 2018

(54) LABORATORY SAMPLE DISTRIBUTION SYSTEM AND LABORATORY AUTOMATION SYSTEM

(71) Applicant: Roche Diagnostics Operations, Inc., Indianapolis, IN (US)

(72) Inventors: Hans Schneider, Schwaikheim (DE); Christian Riether, Muehltal (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 15/436,051

(22) Filed: Feb. 17, 2017

(65) Prior Publication Data
US 2017/0160299 A1    Jun. 8, 2017

Related U.S. Application Data

(63) Continuation of application No. PCT/EP2015/075175, filed on Oct. 29, 2015.

(30) Foreign Application Priority Data

Nov. 3, 2014    (EP) .................................. 14191456.6

(51) Int. Cl.
*B65G 54/02*    (2006.01)
*G01N 35/04*    (2006.01)
(Continued)

(52) U.S. Cl.
CPC .............. *G01N 35/04* (2013.01); *B65G 54/02* (2013.01); *H01F 5/04* (2013.01); *H01F 7/206* (2013.01);
(Continued)

(58) Field of Classification Search
CPC ........... B65G 54/02; B65G 51/02; H01F 5/04; H01R 24/58; H01R 12/71; G01N 35/04
(Continued)

(56) References Cited

U.S. PATENT DOCUMENTS 2,922,138 A    1/1960    Comins, Jr.
3,273,727 A    9/1966    Rogers et al.
(Continued)

FOREIGN PATENT DOCUMENTS

CN    201045617 Y    4/2008
CN    102109530 A    6/2011
(Continued)

OTHER PUBLICATIONS

Anonymous, 3.5 mm PCB mount male plug, Electrical Engineering Stach Exchange, Oct. 24, 2013, URL:http://electronics. stackexchange.com/exchange.com/questions/86367/3-5mm-pcb-mount-male-plug, retrieved from the internet Oct. 4, 2015, 2 pps.
(Continued)

*Primary Examiner* — James R Bidwell
(74) *Attorney, Agent, or Firm* — Roche Diagnostics Operations, Inc.

(57) ABSTRACT

A laboratory sample distribution system and to a laboratory automation system comprising a printed circuit board arrangement and a coil are presented. The printed circuit board arrangement and the coil are configured such that assembly and maintenance of the laboratory automation system are greatly simplified.

13 Claims, 3 Drawing Sheets

(51) Int. Cl.
  *H01F 5/04*  (2006.01)
  *H05K 3/32*  (2006.01)
  *H01F 7/20*  (2006.01)

(52) U.S. Cl.
  CPC ..... *H05K 3/325* (2013.01); *G01N 2035/0477* (2013.01); *H05K 2201/1003* (2013.01); *H05K 2201/10189* (2013.01); *H05K 2201/10424* (2013.01); *H05K 2201/10962* (2013.01)

(58) Field of Classification Search
  USPC ....................................................... 198/805
  See application file for complete search history.

(56) References Cited

U.S. PATENT DOCUMENTS

| | | | |
|---|---|---|---|
| 3,653,485 | A | 4/1972 | Donlon |
| 3,901,656 | A | 8/1975 | Durkos et al. |
| 4,150,666 | A | 4/1979 | Brush |
| 4,395,164 | A | 7/1983 | Beltrop et al. |
| 4,544,068 | A | 10/1985 | Cohen |
| 4,771,237 | A | 9/1988 | Daley |
| 5,120,506 | A | 6/1992 | Saito et al. |
| 5,295,570 | A | 3/1994 | Grecksch et al. |
| 5,309,049 | A | 5/1994 | Kawada et al. |
| 5,523,131 | A | 6/1996 | Isaacs et al. |
| 5,530,345 | A | 6/1996 | Murari et al. |
| 5,636,548 | A | 6/1997 | Dunn et al. |
| 5,641,054 | A | 6/1997 | Mori et al. |
| 5,651,941 | A | 7/1997 | Stark et al. |
| 5,720,377 | A | 2/1998 | Lapeus et al. |
| 5,735,387 | A | 4/1998 | Polaniec et al. |
| 5,788,929 | A | 8/1998 | Nesti |
| 6,045,319 | A | 4/2000 | Uchida et al. |
| 6,062,398 | A | 5/2000 | Thalmayr |
| 6,141,602 | A | 10/2000 | Igarashi et al. |
| 6,151,535 | A | 11/2000 | Ehlers |
| 6,184,596 | B1 | 2/2001 | Ohzeki |
| 6,191,507 | B1 | 2/2001 | Peltier et al. |
| 6,206,176 | B1 | 3/2001 | Blonigan et al. |
| 6,255,614 | B1 | 7/2001 | Yamakawa et al. |
| 6,260,360 | B1 | 7/2001 | Wheeler |
| 6,279,728 | B1 | 8/2001 | Jung et al. |
| 6,293,750 | B1 | 9/2001 | Cohen et al. |
| 6,429,016 | B1 | 8/2002 | McNeil |
| 6,444,171 | B1 | 9/2002 | Sakazume et al. |
| 6,571,934 | B1 | 6/2003 | Thompson et al. |
| 7,028,831 | B2 | 4/2006 | Veiner |
| 7,078,082 | B2 | 7/2006 | Adams |
| 7,122,158 | B2 | 10/2006 | Itoh |
| 7,278,532 | B2 | 10/2007 | Martin |
| 7,326,565 | B2 | 2/2008 | Yokoi et al. |
| 7,425,305 | B2 | 9/2008 | Itoh |
| 7,428,957 | B2 | 9/2008 | Schaefer |
| 7,578,383 | B2 | 8/2009 | Itoh |
| 7,597,187 | B2 | 10/2009 | Bausenwein et al. |
| 7,850,914 | B2 | 12/2010 | Veiner et al. |
| 7,858,033 | B2 | 12/2010 | Itoh |
| 7,875,254 | B2 | 1/2011 | Garton et al. |
| 7,939,484 | B1 | 5/2011 | Loeffler et al. |
| 8,240,460 | B1 | 8/2012 | Bleau et al. |
| 8,281,888 | B2 | 10/2012 | Bergmann |
| 8,502,422 | B2 | 8/2013 | Lykkegaard |
| 8,796,186 | B2 | 8/2014 | Shirazi |
| 9,097,691 | B2 | 8/2015 | Onizawa et al. |
| 9,187,268 | B2 | 11/2015 | Denninger et al. |
| 9,211,543 | B2 | 12/2015 | Ohga et al. |
| 9,239,335 | B2 | 1/2016 | Heise et al. |
| 9,423,410 | B2 | 8/2016 | Buehr |
| 9,423,411 | B2 | 8/2016 | Riether |
| 9,567,167 | B2 | 2/2017 | Sinz |
| 9,575,086 | B2 | 2/2017 | Heise et al. |
| 9,593,970 | B2 | 3/2017 | Sinz |
| 9,598,243 | B2 | 3/2017 | Denninger et al. |
| 9,658,241 | B2 | 5/2017 | Riether et al. |
| 9,664,703 | B2 * | 5/2017 | Heise ..................... G01N 35/04 |
| 9,791,468 | B2 * | 10/2017 | Riether ................... G01N 35/10 |
| 2002/0009391 | A1 | 1/2002 | Marquiss et al. |
| 2002/0096938 | A1 | 7/2002 | Wojciechowski |
| 2003/0092185 | A1 | 5/2003 | Qureshi et al. |
| 2004/0050836 | A1 | 3/2004 | Nesbitt et al. |
| 2004/0084531 | A1 | 5/2004 | Itoh |
| 2005/0061622 | A1 | 3/2005 | Martin |
| 2005/0109580 | A1 | 5/2005 | Thompson |
| 2005/0194333 | A1 | 9/2005 | Veiner et al. |
| 2005/0196320 | A1 | 9/2005 | Veiner et al. |
| 2005/0226770 | A1 | 10/2005 | Allen et al. |
| 2005/0242963 | A1 | 11/2005 | Oldham et al. |
| 2005/0247790 | A1 | 11/2005 | Itoh |
| 2005/0260101 | A1 | 11/2005 | Nauck et al. |
| 2005/0271555 | A1 | 12/2005 | Itoh |
| 2006/0000296 | A1 | 1/2006 | Salter |
| 2006/0047303 | A1 | 3/2006 | Ortiz et al. |
| 2006/0219524 | A1 | 10/2006 | Kelly et al. |
| 2006/0245630 | A1 | 11/2006 | Zahniser et al. |
| 2007/0116611 | A1 | 5/2007 | DeMarco |
| 2007/0210090 | A1 | 9/2007 | Sixt et al. |
| 2007/0248496 | A1 | 10/2007 | Bondioli et al. |
| 2007/0276558 | A1 | 11/2007 | Kim |
| 2008/0012511 | A1 | 1/2008 | Ono |
| 2008/0029368 | A1 | 2/2008 | Komori |
| 2008/0056328 | A1 | 3/2008 | Rund et al. |
| 2008/0131961 | A1 | 6/2008 | Crees et al. |
| 2009/0004732 | A1 | 1/2009 | LaBarre et al. |
| 2009/0022625 | A1 | 1/2009 | Lee et al. |
| 2009/0081771 | A1 | 3/2009 | Breidford et al. |
| 2009/0128139 | A1 | 5/2009 | Drenth et al. |
| 2009/0142844 | A1 | 6/2009 | Le Comte |
| 2009/0180931 | A1 | 7/2009 | Silbert et al. |
| 2009/0322486 | A1 | 12/2009 | Gerstel |
| 2010/0000250 | A1 | 1/2010 | Sixt |
| 2010/0152895 | A1 | 6/2010 | Dai |
| 2010/0175943 | A1 | 7/2010 | Bergmann |
| 2010/0186618 | A1 | 7/2010 | King et al. |
| 2010/0255529 | A1 | 10/2010 | Cocola et al. |
| 2010/0300831 | A1 | 12/2010 | Pedrazzini |
| 2010/0312379 | A1 | 12/2010 | Pedrazzini |
| 2011/0050213 | A1 | 3/2011 | Furukawa |
| 2011/0124038 | A1 | 5/2011 | Bishop et al. |
| 2011/0172128 | A1 | 7/2011 | Davies et al. |
| 2011/0186406 | A1 | 8/2011 | Kraus et al. |
| 2011/0250785 | A1 | 10/2011 | Reid |
| 2011/0287447 | A1 | 11/2011 | Norderhaug et al. |
| 2012/0037696 | A1 | 2/2012 | Lavi |
| 2012/0129673 | A1 | 5/2012 | Fukugaki et al. |
| 2012/0178170 | A1 | 7/2012 | Van Praet |
| 2012/0211645 | A1 | 8/2012 | Tullo et al. |
| 2012/0275885 | A1 | 11/2012 | Furrer et al. |
| 2012/0282683 | A1 | 11/2012 | Mototsu |
| 2012/0295358 | A1 | 11/2012 | Ariff et al. |
| 2012/0310401 | A1 | 12/2012 | Shah |
| 2013/0034410 | A1 | 2/2013 | Heise et al. |
| 2013/0126302 | A1 | 5/2013 | Johns et al. |
| 2013/0153677 | A1 | 6/2013 | Leen et al. |
| 2013/0180824 | A1 | 7/2013 | Kleinikkink et al. |
| 2013/0263622 | A1 | 10/2013 | Mullen et al. |
| 2013/0322992 | A1 | 12/2013 | Pedrazzini |
| 2014/0170023 | A1 | 6/2014 | Saito et al. |
| 2014/0234065 | A1 | 8/2014 | Heise et al. |
| 2014/0234949 | A1 | 8/2014 | Wasson et al. |
| 2014/0234978 | A1 * | 8/2014 | Heise ..................... B65G 54/02 |
| | | | 436/48 |
| 2015/0014125 | A1 | 1/2015 | Hecht |
| 2015/0241457 | A1 | 8/2015 | Miller |
| 2015/0273468 | A1 | 10/2015 | Croquette et al. |
| 2015/0273691 | A1 | 10/2015 | Pollack |
| 2015/0276775 | A1 | 10/2015 | Mellars et al. |
| 2015/0276776 | A1 | 10/2015 | Riether |
| 2015/0276777 | A1 | 10/2015 | Riether et al. |
| 2015/0276778 | A1 | 10/2015 | Riether et al. |
| 2015/0276782 | A1 | 10/2015 | Riether |
| 2016/0003859 | A1 | 1/2016 | Wenczel et al. |
| 2016/0025756 | A1 | 1/2016 | Pollack et al. |
| 2016/0054341 | A1 | 2/2016 | Edelmann |

(56) References Cited

U.S. PATENT DOCUMENTS

| | | |
|---|---|---|
| 2016/0077120 A1 | 3/2016 | Riether |
| 2016/0097786 A1 | 4/2016 | Malinowski et al. |
| 2016/0229565 A1 | 8/2016 | Margner |
| 2016/0274137 A1 | 9/2016 | Baer |
| 2016/0282378 A1 | 9/2016 | Malinowski et al. |
| 2016/0341750 A1 | 11/2016 | Sinz et al. |
| 2016/0341751 A1 | 11/2016 | Huber et al. |
| 2017/0059599 A1 | 3/2017 | Riether |
| 2017/0096307 A1 | 4/2017 | Mahmudimanesh et al. |
| 2017/0097372 A1 | 4/2017 | Heise et al. |
| 2017/0101277 A1 | 4/2017 | Malinowski |
| 2017/0108522 A1 | 4/2017 | Baer |
| 2017/0131307 A1 | 5/2017 | Pedain |
| 2017/0131309 A1 | 5/2017 | Pedain |
| 2017/0131310 A1 | 5/2017 | Volz et al. |
| 2017/0138971 A1 | 5/2017 | Heise et al. |
| 2017/0168079 A1 | 6/2017 | Sinz |
| 2017/0174448 A1 | 6/2017 | Sinz |
| 2017/0184622 A1 | 6/2017 | Sinz et al. |
| 2017/0248623 A1 | 8/2017 | Kaeppeli et al. |
| 2017/0248624 A1 | 8/2017 | Kaeppeli et al. |
| 2017/0363608 A1 | 12/2017 | Sinz |

FOREIGN PATENT DOCUMENTS

| | | |
|---|---|---|
| DE | 3539037 A1 | 6/1987 |
| DE | 3909786 A1 | 9/1990 |
| DE | 4122983 A1 | 10/1992 |
| DE | 102012000665 A1 | 8/2012 |
| DE | 102011090044 A1 | 7/2013 |
| EP | 0601213 A1 | 10/1992 |
| EP | 0775650 A1 | 5/1997 |
| EP | 0916406 A2 | 5/1999 |
| EP | 1122194 A1 | 8/2001 |
| EP | 1524525 A1 | 4/2005 |
| EP | 2119643 A1 | 11/2009 |
| EP | 2148117 A1 | 1/2010 |
| EP | 2327646 A1 | 6/2011 |
| EP | 2447701 A2 | 5/2012 |
| EP | 2500871 A1 | 9/2012 |
| EP | 2502675 B1 | 2/2014 |
| EP | 2887071 A1 | 6/2015 |
| GB | 2165515 A | 4/1986 |
| JP | S56-147209 A | 11/1981 |
| JP | 60-223481 A | 11/1985 |
| JP | 61-081323 A | 4/1986 |
| JP | S61-069604 A | 4/1986 |
| JP | S61-094925 A | 5/1986 |
| JP | S61-174031 A | 8/1986 |
| JP | S61-217434 A | 9/1986 |
| JP | S62-100161 A | 5/1987 |
| JP | S63-31918 A | 2/1988 |
| JP | S63-48169 A | 2/1988 |
| JP | S63-82433 U | 5/1988 |
| JP | S63-290101 A | 11/1988 |
| JP | 1148966 A | 6/1989 |
| JP | H01-266860 A | 10/1989 |
| JP | H02-87903 A | 3/1990 |
| JP | 03-112393 A | 5/1991 |
| JP | 03-192013 A | 8/1991 |
| JP | H03-38704 Y2 | 8/1991 |
| JP | H04-127063 A | 4/1992 |
| JP | H05-69350 A | 3/1993 |
| JP | H05-142232 A | 6/1993 |
| JP | H05-180847 A | 7/1993 |
| JP | 06-26808 A | 2/1994 |
| JP | H06-148198 A | 5/1994 |
| JP | 06-156730 A | 6/1994 |
| JP | 06-211306 A | 8/1994 |
| JP | 07-228345 A | 8/1995 |
| JP | 07-236838 A | 9/1995 |
| JP | H07-301637 A | 11/1995 |
| JP | H09-17848 A | 1/1997 |
| JP | H11-083865 A | 3/1999 |
| JP | H11-264828 A | 9/1999 |
| JP | H11-304812 A | 11/1999 |
| JP | H11-326336 A | 11/1999 |
| JP | 2000-105243 A | 4/2000 |
| JP | 2000-105246 A | 4/2000 |
| JP | 2001-124786 A | 5/2001 |
| JP | 2001-240245 A | 9/2001 |
| JP | 2005-001055 A | 1/2005 |
| JP | 2005-249740 A | 9/2005 |
| JP | 2006-106008 A | 4/2006 |
| JP | 2007-309675 A | 11/2007 |
| JP | 2007-314262 A | 12/2007 |
| JP | 2007-322289 A | 12/2007 |
| JP | 2009-036643 A | 2/2009 |
| JP | 2009-062188 A | 3/2009 |
| JP | 2009-145188 A | 7/2009 |
| JP | 2009-300402 A | 12/2009 |
| JP | 2010-243310 A | 10/2010 |
| JP | 2013-172009 A | 2/2013 |
| JP | 2013-190400 A | 9/2013 |
| SU | 685591 A1 | 9/1979 |
| WO | 1994/013034 A1 | 6/1994 |
| WO | 1996/036437 A1 | 11/1996 |
| WO | 2003/042048 A3 | 5/2003 |
| WO | 2007/024540 A1 | 3/2007 |
| WO | 2008/133708 A1 | 11/2008 |
| WO | 2009/002358 A1 | 12/2008 |
| WO | 2009/043865 A2 | 4/2009 |
| WO | 2010/042722 A1 | 4/2010 |
| WO | 2012170636 A1 | 7/2010 |
| WO | 2010/087303 A1 | 8/2010 |
| WO | 2010/129715 A1 | 11/2010 |
| WO | 2012/158520 A1 | 11/2012 |
| WO | 2012/158541 A1 | 11/2012 |
| WO | 2013/100524 A1 | 7/2013 |
| WO | 2013/152089 A1 | 10/2013 |
| WO | 2013/169778 A1 | 11/2013 |
| WO | 2013/177163 A1 | 11/2013 |
| WO | 2014/059134 A1 | 4/2014 |
| WO | 2014/071214 A1 | 5/2014 |

OTHER PUBLICATIONS

International Search Report dated Dec. 11, 2015, in Application No. PCT/EP2015/075175, 4 pages.

* cited by examiner

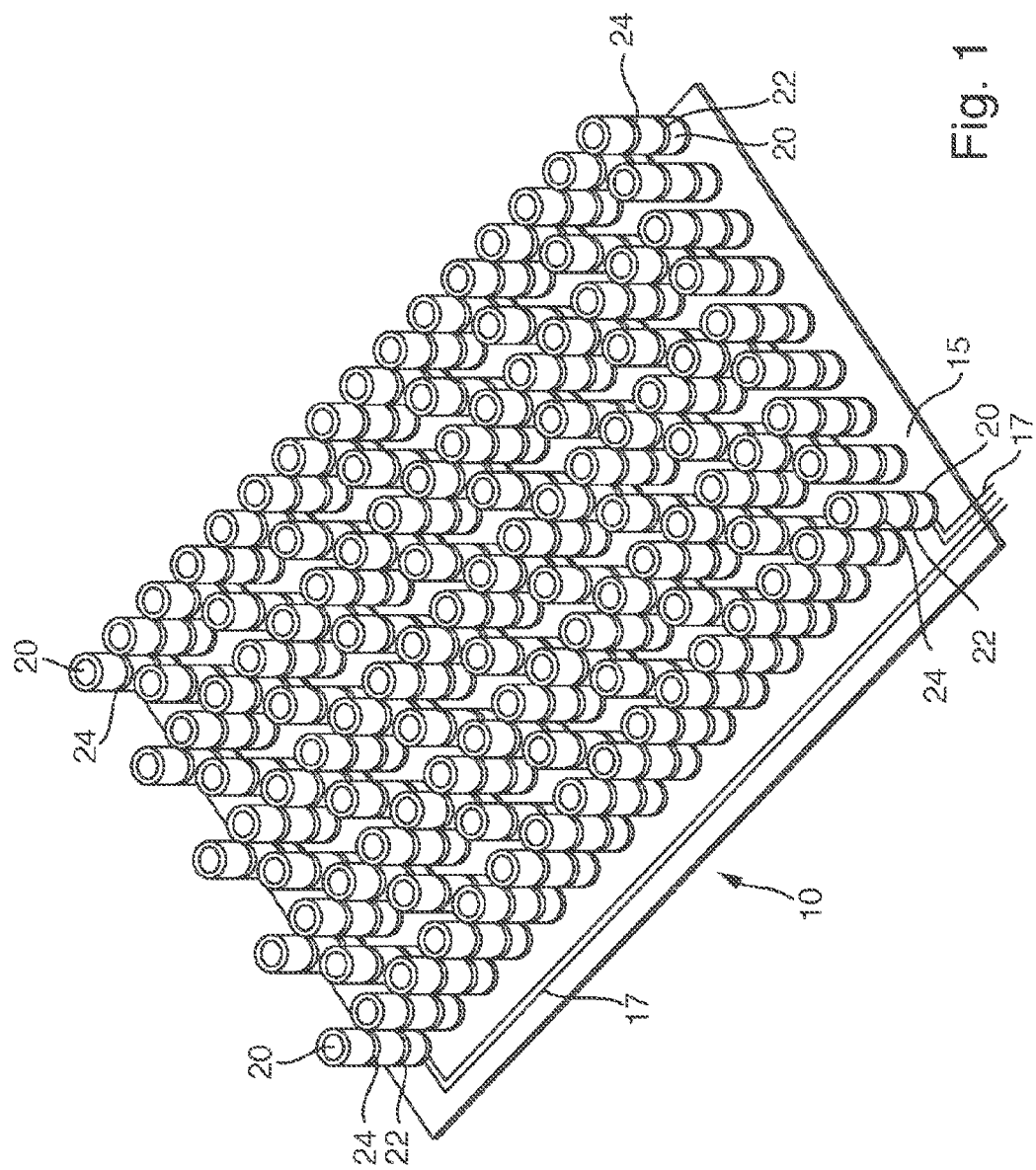

LABORATORY SAMPLE DISTRIBUTION SYSTEM AND LABORATORY AUTOMATION SYSTEM

CROSS-REFERENCE TO RELATED APPLICATIONS

This application is a continuation of PCT/EP2015/075175 filed Oct. 29, 2015, which is based on and claims priority to EP 14191455.6, filed Nov. 3, 2014, which is hereby incorporated by reference.

BACKGROUND

The present disclosure relates to a laboratory sample distribution system and to a laboratory automation system comprising such a laboratory sample distribution system.

Laboratory automation systems typically comprise a number of laboratory stations, such as pre-analytical, analytical and/or post-analytical stations, and a laboratory sample distribution system. The laboratory stations can typically be used in order to analyze medical samples such as blood samples. The laboratory stations can also be used in order to perform other tasks like decapping or centrifugation.

The laboratory sample distribution system can typically be used in order to transport sample containers containing samples to be analyzed between the laboratory stations. A typical laboratory sample distribution system discloses a number of sample container carriers moving on a transport plane driven by electro-magnetic actuators being positioned below the transport plane and being controlled by a control unit. Usage of such a laboratory sample distribution system significantly increases throughput of a laboratory automation system and minimizes the need for manual interaction.

In typical laboratory sample distribution systems, the electro-magnetic actuators are embodied as coils. In order to provide for the possibility to energize a coil, each coil is connected via a connector to respective complementary connectors e.g. on a printed circuit board. However, it has been discovered that mounting such connectors imposes a significant risk of producing false or unreliable electrical connections.

Therefore, there is a need for a laboratory sample distribution system and a laboratory automation system comprising a laboratory sample distribution system providing simplified electrical connections.

SUMMARY

According to the present disclosure, a laboratory sample distribution system is presented. The laboratory sample distribution system can comprise at least one printed circuit board arrangement. The at least one printed circuit board arrangement can comprise a printed circuit board having a number of conductive lines and a number of tubular sleeves. Each sleeve can be mounted on the printed circuit board. Each sleeve can comprise a first electric contact and a second electric contact. The first electric contact and the second electric contact can be positioned at an outer surface of the sleeve and the first electric contact and the second electric contact can be connected to corresponding conductive lines of the number of conductive lines. The laboratory sample distribution system can also comprise a number of coils. Each coil can comprise a winding of an electric conductor. The winding can have a first terminal and a second terminal. Each coil can also comprise a tubular casing. The tubular casing can house the winding. The tubular casing can have an inner surface defining a hollow cylindrical interior. Each coil can also comprise a first electric contact and a second electric contact. The first electric contact can be electrically connected to the first terminal and the second electric contact can be electrically connected to the second terminal. The first electric contact and the second electric contact can be arranged at the inner surface of the casing. Each coil of the number of coils can be imposed on a corresponding sleeve of the number of sleeves. The first electric contact of each coil can abut the first electric contact of the sleeve on which it is imposed and the second electric contact of each coil can abut the second electric contact of the sleeve on which it is imposed. The laboratory sample distribution system can also comprise a number of ferromagnetic cores. Each ferromagnetic core can be at least partially comprised in a corresponding sleeve of the number of sleeves. The laboratory sample distribution system can also comprise a transport plane arranged above the printed circuit board arrangement, above the coils, and above the ferromagnetic cores.

Accordingly, it is a feature of the embodiments of the present disclosure to provide for a laboratory sample distribution system and a laboratory automation system comprising a laboratory sample distribution system providing simplified electrical connections. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which:

FIG. 1 illustrates a printed circuit board arrangement according to an embodiment of the present disclosure.

DETAILED DESCRIPTION

Figure 2A:
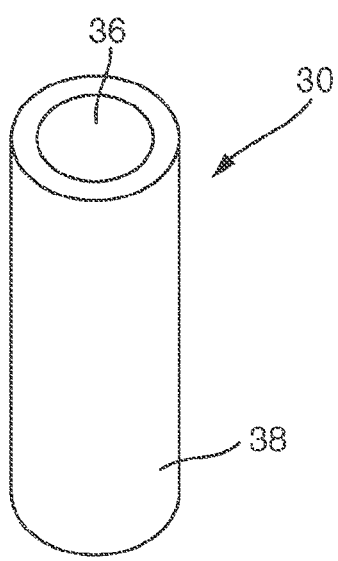
FIG. 2a illustrates a coil according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A laboratory sample distribution system is presented. The laboratory sample distribution system can comprise at least one printed circuit board arrangement, a number of coils, a number of ferromagnetic cores and a transport plane arranged above the printed circuit board arrangement, above the coils and above the ferromagnetic cores.

Each ferromagnetic core can be at least partially comprised in a corresponding sleeve of the number of sleeves.

The ferromagnetic cores can enhance magnetic fields generated by the coils. Typically, the ferromagnetic cores can be inserted into the sleeves.

The transport plane can provide a surface on which sample container carriers transporting sample containers can move. The sample container carriers can be driven by magnetic fields generated by the coils.

The printed circuit board arrangement can comprise a printed circuit board having a number (such as, for example, 2 to 2000) of electrically conductive lines.

The printed circuit board arrangement can further comprise a number (such as, for example, 2 to 256) of tubular sleeves, which may alternatively be denoted as hulls, jackets, or cartridges. It can be noted that the word "tubular" is not necessarily to be understood such that the sleeves can have a circular cross-section. For example, the sleeves can also have a rectangular, quadratic or triangular cross-section.

Each sleeve can be mounted, or arranged, on the printed circuit board. Furthermore, each sleeve can comprise a first electric contact and a second electric contact. The electric contacts can be positioned at an outer surface of the sleeve and each electric contact can be electrically connected to a respective conductive line of the number of conductive lines. The sleeve may comprise conductor paths electrically connecting a corresponding conductive line of the printed circuit board to a corresponding electric contact. The conductor paths may e.g. extend vertically from a terminal point in contact with the conductive line to the corresponding electric contact. The conductor paths may extend electrically isolated, e.g. in an inner layer of a corresponding sleeve.

Self-evidently, the first electric contact and the second electric contact can be electrically isolated from one another. Further, the conductor paths of the sleeve can be electrically isolated from one another. The electrical isolation may e.g. be realized by electrical isolators between the first electric contact and the second electric contact and/or between the conductor paths. The sleeve may comprise a base body made of electrically non-conductive material. The first electric contact and the second electric contact and/or the conductor paths can be formed as conductive layers and/or strips on the base body.

It can be noted that the sleeves can be positioned above the printed circuit board, or that the sleeves can be positioned below the printed circuit board. Examples will be given further below.

Each coil can be imposed on a corresponding sleeve. The number of coils typically can correspond to the number of sleeves. Imposing a coil on a sleeve can denote that a hollow cylindrical interior of the coil can be filled by the respective sleeve. The coil can be imposed such that it can abut the printed circuit board.

The first electric contact of each coil can abut and thus electrically contact the first electric contact of the sleeve on which it is imposed and the second electric contact of each coil can abut and thus electrically contact the second electric contact of the sleeve on which it is imposed. Typically, an electrical connection can thus be formed between the respective first electric contacts and the respective second electric contacts.

By the printed circuit board arrangement, it can be possible to simplify an electrical connection between the coils and the printed circuit board because the coils can easily be imposed over the sleeves. Electric connections can be accomplished just by providing complementary electric contacts at an inner surface of the coil such that they can abut and thus electrically contact the electric contacts of the respective sleeve.

According to an embodiment, the first electric contact can be arranged as a cylindrical ring made of electrically conductive material. According to another embodiment, the second electric contact can be arranged as a cylindrical ring made of electrically conductive material. It can be noted that these two embodiments can be combined, so that both the first and the second electric contact can be arranged as a cylindrical ring made of electrically conductive material. The electric contacts can provide for an electrically conductive surface around a circumference of a respective sleeve. This can omit a need to impose a coil having a specific orientation.

According to an embodiment, a distance between the printed circuit board and the first electric contact can be identical to a distance between a longitudinal end of the sleeve opposite to the printed circuit board and the second electric contact.

According to an embodiment, the sleeves can be detachably mounted on the printed circuit board by using gudgeons and corresponding grooves. This can allow for an easy fixation and detaching of the sleeves at the printed circuit board. The gudgeons can be embodied at the sleeves and the grooves can be embodied at the printed circuit board, or vice versa.

According to an embodiment, each sleeve can comprise an electric isolation between a hollow interior and the electric contacts. This can allow for a placement of ferromagnetic cores made of electrically conductive material inside the sleeves without having a risk of a short-circuiting between such a ferromagnetic core and one or both of the electric contacts of the sleeve.

According to an embodiment, the printed circuit board can comprise a number of position sensors. These position sensors can be implemented as Hall-sensors. Typically, each position sensor can be assigned to one of the sleeves. Such position sensors can be used in order to detect positions of sample container carriers moving on a transport plane above the printed circuit board. This embodiment can be useful if the printed circuit board is arranged above the sleeves. Such a configuration can allow for a close proximity between the transport plane and the printed circuit board, which can be useful in order to minimize a number of electric components because the position sensors can readily be arranged on the printed circuit board.

According to an embodiment, a number of positions can be defined on the printed circuit board in a checkered manner. Each sleeve can be located on one such position such that in each second line of positions each second position can be left without a sleeve.

Such an embodiment has been proven useful for typical laboratory sample distribution systems because lines with a sleeve at each position can be used at transport paths for sample container carriers, and lines having only a sleeve at each second position can be used as spacers between such transport paths. It can be noted that typically one coil can be imposed over each sleeve in an assembled laboratory sample distribution system.

According to an embodiment, a number of bores can be formed in the printed circuit board such that each bore can be assigned to one of the sleeves. This configuration can especially allow for an arrangement in which the sleeves can be positioned above the printed circuit board. In such a configuration, ferromagnetic cores can typically be put through such bores from below the printed circuit board.

Each coil can comprise a winding of an electric conductor. The winding can have a first and a second electric terminal.

Each coil can further comprise a tubular casing (coil body or coil bobbin) housing the winding and defining a hollow cylindrical interior.

Each coil can comprise a first electric contact and a second electric contact. The first electric contact can be electrically connected to the first terminal and the second electric contact can be electrically connected to the second terminal. The first electric contact and the second electric contact of the coil can be arranged at an inner surface area of the casing. The inner surface area can define the cylindrical interior. The inner surface area can surround the cylindrical interior.

By a coil, an assembly of a laboratory sample distribution system can be significantly simplified. A coil can be imposed over a corresponding sleeve. A coil can be used in connection with a circuit board arrangement as discussed above.

According to an embodiment, the first electric contact of the coil can be configured as a spring contact. According to another embodiment, the second electric contact of the coil can be configured as a spring contact. It can be noted that these two embodiments can be combined. Alternatively, the first electric contact and/or the second electric contact of the sleeves can be configured as a respective spring contact. Spring contacts can provide for a generally better electric contact.

According to an embodiment, a distance between a first longitudinal end of the coil and the first electric contact can be identical to a distance between a second longitudinal end of the coil opposite to the first longitudinal end and the second electric contact. Such an embodiment can be useful in connection with the corresponding configuration of the electric contacts of the sleeves as discussed above. This configuration can provide for the possibility to impose a coil on a respective sleeve such that it may not matter which longitudinal end of the coil faces towards the printed circuit board. This can simplify assembly of a laboratory sample distribution system.

The laboratory sample distribution system may comprise a number of magnetic bars. Each magnetic bar can comprise a number of magnetic cores. Each magnetic core can at least partially be comprised in a sleeve. Such magnetic bars can simplify assembly of the cores, because a magnetic bar can provide for a plurality of cores. In addition, such a magnetic bar can enhance magnetic coupling between neighboring cores and thus enhance system efficiency.

According to an embodiment, some, or all, of the sleeves can comprise a gudgeon caught in a groove of the coil imposed over the sleeve. According to an alternative embodiment, some, or all, of the coils can comprise a gudgeon caught in a groove of the sleeve over which the coil can be imposed. Such embodiments can allow for a certain, typically detachable fixation of the coils at the sleeves.

According to an embodiment, the laboratory sample distribution system can comprise a number of sample container carriers each comprising at least one magnetically active device. The sample container carriers can be adapted to move on the transport plane. The laboratory sample distribution system can further comprise a control unit configured to control the movement of the sample container carriers on the transport plane by driving the coils as electro-magnetic actuators such that the sample container carriers can move along corresponding transport paths. The control unit can be configured to control movement of the sample container carriers in two dimensions.

A laboratory automation system is also presented. The laboratory automation system can comprise a number of a pre-analytical, analytical and/or post-analytical (laboratory) stations and a laboratory sample distribution system as described above adapted to transport the sample container carriers and/or sample containers between the stations. The stations may be arranged adjacent to the laboratory sample distribution system.

Pre-analytical stations may be adapted to perform any kind of pre-processing of samples, sample containers and/or sample container carriers.

Analytical stations may be adapted to use a sample or part of the sample and a reagent to generate a measuring signal, the measuring signal indicating if and in which concentration, if any, an analyte exists.

Post-analytical stations may be adapted to perform any kind of post-processing of samples, sample containers and/or sample container carriers.

The pre-analytical, analytical and/or post-analytical stations may comprise at least one of a decapping station, a recapping station, an aliquot station, a centrifugation station, an archiving station, a pipetting station, a sorting station, a tube type identification station, a sample quality determining station, an add-on buffer station, a liquid level detection station, and a sealing/desealing station.

Referring initially to FIG. 1, FIG. 1 shows a printed circuit board arrangement 10 for a laboratory sample distribution system. The printed circuit board arrangement 10 can comprise a printed circuit board 15 and a number of sleeves 20. Each of the sleeves 20 can be fixed at a specific position on the printed circuit board 15.

Each sleeve can comprise a first electric contact 22 and a second electric contact 24. The first electric contact 22 can be positioned with a distance above the printed circuit board 15 that can be equal to a distance between an upper end of the sleeve 20 and the second electric contact 24.

The printed circuit board 15 can comprise a number of conductive lines, or strip, conductors 17. The conductive lines 17 can be arranged such that electric voltage and current can be specifically applied to the electric contacts 22, 24 of each sleeve 20. For that purpose, the electric contacts 22, 24 can each be connected with a respective conductive line 17. The conductive lines 17 can, for example, lead to a central control unit. In FIG. 1, only a selection of such conductive lines 17 is shown for reasons of simplicity of illustration. In practice, each electric contact 22, 24 of each sleeve may have its own conductive line 17.

FIG. 2a shows a coil 30 that can be imposed on the sleeves 20 shown in FIG. 1. The coil 30 can have a tubular casing 38 forming a coil body. The tubular casing 38 can have an inner surface 36 defining a hollow cylindrical interior.

Figure 2B:
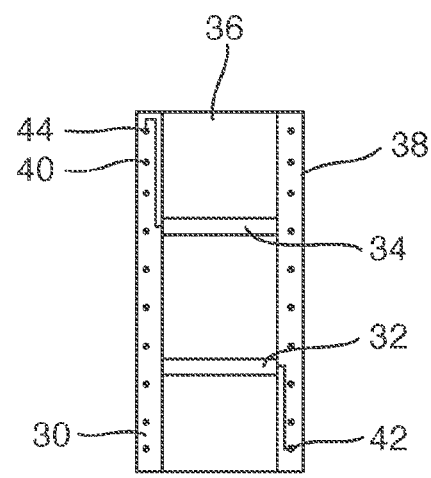
FIG. 2b illustrates the coil of FIG. 2a in a cross-sectional view according to an embodiment of the present disclosure.

FIG. 2b shows a cross-sectional view through the coil 30 of FIG. 2a. The coil 30 can comprise a first electric contact 32 and a second electric contact 34 that can be arranged at the inner surface 36. The first electric contact 32 and the second electric contact 34 can be embodied as spring contacts that can extend around a circumference of the inner surface 36.

Around the inner surface 36 inside the tubular casing 38, a winding 40 can be arranged. The winding 40 can extend over a longitudinal extension of the coil 30. The winding 40 can have a first terminal 42 and a second terminal 44. The first terminal 42 can be connected with the first electric contact 32 of the coil 30. The second terminal 44 can be connected with the second electric contact 34 of the coil 30.

The first electric contact 32 can be positioned with a distance to a first longitudinal end of the coil 30 that can be identical to a distance between the second electric contact 34 and a second longitudinal end of the coil 30. The first electric contact 32 can be positioned with the same distance from the first longitudinal end of the coil 30 as the distance between the first electric contact 22 of the sleeve 20 and the printed circuit board 15. A diameter of the inner surface area 36 of the coil 30 can be only slightly larger than the diameter of the sleeves 20. Thus, the coil 30 can be imposed on any of the sleeves 20 such that an electric connection can be made between the respective first electric contacts 22, 32 and the respective second electric contacts 24, 34 of the sleeve 20 and the coil 30, respectively.

It can be noted that it can be irrespective if the coil 30 is imposed on the sleeve 20 such that the first electric contact 32 can be positioned below the second electric contact 34, or opposite. If the second electric contact 34 of the coil 30 is positioned below the first electric contact 32, the first electric contact 22 of the sleeve 20 can be in electric contact with the second electric contact 34 of the coil 30 and the second electric contact 24 of the sleeve 20 can be in electric contact with the first electric contact 32 of the coil 30. However, due to the symmetry of the coil 30, a magnetic field generated by the coil 30 when a current is applied via the electric contacts 22, 24 of the sleeve 20 may not be dependent on the direction the coil 30 is imposed on the sleeve 20.

Figure 3:
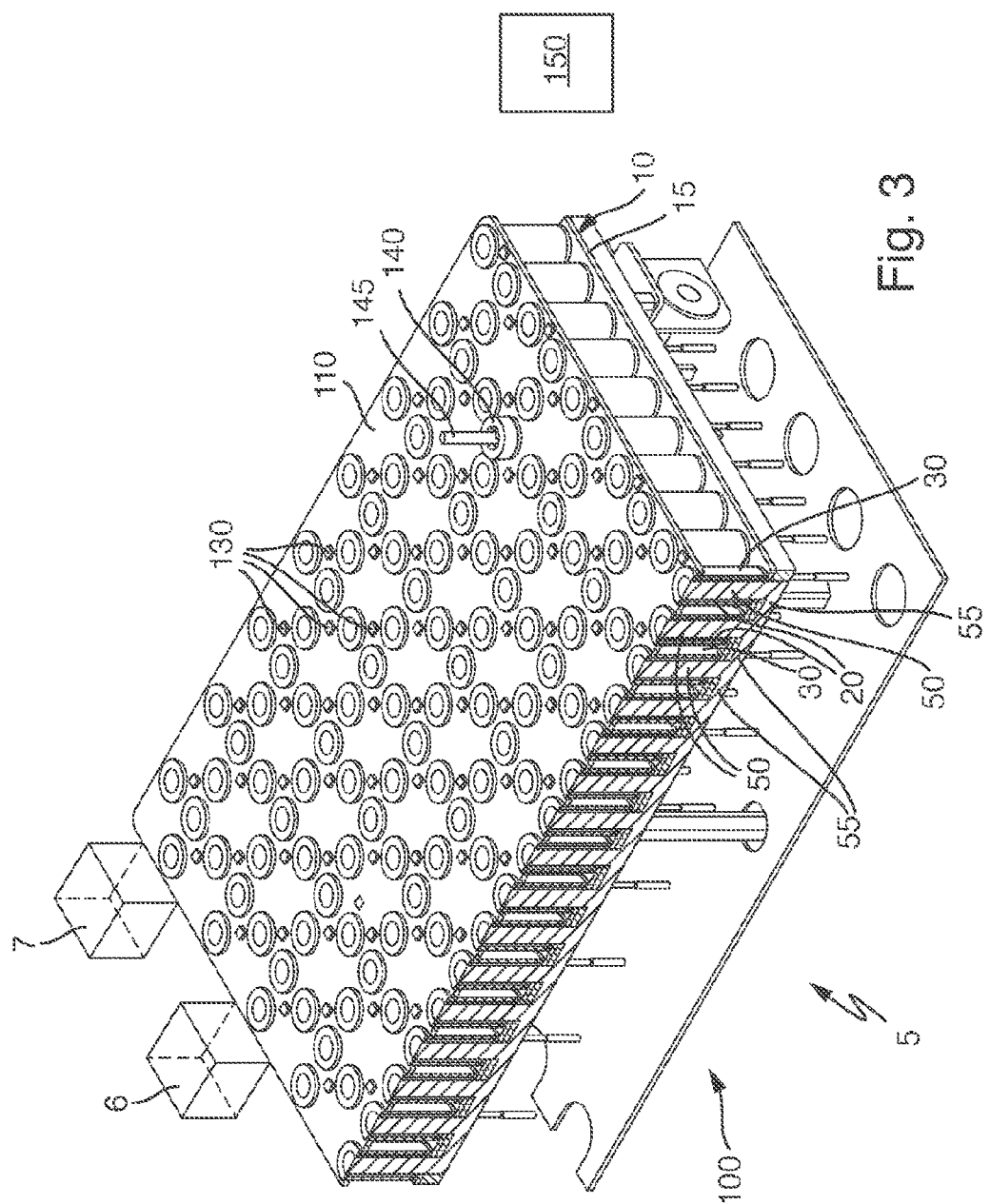
FIG. 3 illustrates a laboratory automation system comprising a laboratory sample distribution system according to an embodiment of the present disclosure.

FIG. 3 shows a laboratory automation system 5 comprising a first laboratory station 6, a second laboratory station 7 and a laboratory sample distribution system 100. The laboratory stations 6, 7 represent a plurality of laboratory stations that are typically comprised by a laboratory automation system.

The laboratory sample distribution system 100 can comprise a transport plane 110, on which a number of sample container carriers 140 can move. Each sample container carrier 140 can carry a sample container 145. It can be noted that a typical laboratory sample distribution system 100 can comprise a plurality of sample container carriers 140 with respective sample containers 145. However, in order to simplify the illustration, only one such sample container carrier 140 with a sample container 145 is shown in FIG. 3.

The laboratory sample distribution system 100 can further comprise a printed circuit board arrangement 10 as shown in FIG. 1. The printed circuit board arrangement 10 can be positioned such that the printed circuit board 15 can be positioned below the sleeves 20.

Above each sleeve 20, there can be imposed a coil 30 as shown in FIGS. 2a and 2b. These coils 30 can serve as electro-magnetic actuators in the laboratory sample distribution system 100.

To each coil 30, a ferromagnetic core 50 can be assigned. The ferromagnetic core 50 can be arranged inside of the respective sleeve 20 on which the coil 30 is imposed. The ferromagnetic core 50 can protrude through respective holes in the printed circuit board 15 from a lower side of the laboratory sample distribution system 100. The core 50 can significantly increase magnetic fields generated by the coils 30.

Neighboring cores 50 can be connected by respective magnetically coupling elements 55 such that the cores 50 and the magnetically coupling elements 55 can form a magnetic bar. This can increase magnetic coupling between respective neighboring cores.

The laboratory sample distribution system 100 can further comprise a number of magnetic sensors 130, which can be embodied as Hall-sensors. These Hall-sensors can be configured to sense a position of a sample container carrier 140. Furthermore, the laboratory sample distribution system 100 can comprise a control unit 150. The control unit 150 can be adapted to control the currents flowing through the coils 30 such that sample container carriers 140 can move along respective transport paths. For that purpose, each sample container carrier 140 can have a magnetically active element in the form of a permanent magnet (not shown). The permanent magnet of each sample container carrier 140 can drive the sample container carrier 140 by the magnetic fields generated by the coils 30.

In order to control the currents of the coils 30, the control unit 150 or respective drivers of the control unit 150 can be electrically connected to the conductive paths 17 of the printed circuit board 15. Due to the electrical connections between the corresponding electric contacts 22, 32 and 24, 34, the control unit 150 can control the currents flowing through the coils 30.

The control unit 150 can receive position signals from the position sensors 130 so that control unit 150 can monitor the positions of the sample container carriers 140.

It can be noted that according to the embodiment shown in FIG. 3 the magnetic sensors 130 may not be implemented directly on the printed circuit board 15. However, in an alternative embodiment, the printed circuit board 15 can be arranged on top of the sleeves 20, such that the magnetic sensors 130 can be arranged directly on the printed circuit board 15.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A laboratory sample distribution system, the laboratory sample distribution system comprising
at least one printed circuit board arrangement, the at least one printed circuit board arrangement comprising,
a printed circuit board having a number of conductive lines, and
a number of tubular sleeves, wherein each sleeve is mounted on the printed circuit board, wherein each sleeve comprises a first electric contact and a second electric contact, and wherein the first electric contact and the second electric contact are positioned at an outer surface of the sleeve and the first electric contact and the second electric contact are connected to corresponding conductive lines of the number of conductive lines;
a number of coils, each coil comprising,
a winding of an electric conductor, wherein the winding has a first terminal and a second terminal,
a tubular casing, wherein the tubular casing houses the winding and wherein the tubular casing has an inner surface defining a hollow cylindrical interior, and
a first coil electric contact and a second coil electric contact, wherein the first coil electric contact is electrically connected to the first terminal and the second coil electric contact is electrically connected to the second terminal, wherein the first coil electric contact and the second coil electric contact are arranged at the inner surface of the casing, wherein each coil of the number of coils is imposed on a corresponding sleeve of the number of sleeves, and wherein the first coil electric contact of each coil abuts the first electric contact of the sleeve on which it is imposed and the second coil electric contact of each coil abuts the second electric contact of the sleeve on which it is imposed;
a number of ferromagnetic cores, wherein each ferromagnetic core is at least partially comprised in a corresponding sleeve of the number of sleeves; and
a transport plane arranged above the printed circuit board arrangement, above the coils, and above the ferromagnetic cores.

2. The laboratory sample distribution system according to claim 1, wherein the first electric contact is arranged as a cylindrical ring made of electrically conductive material.

3. The laboratory sample distribution system according to claim 1, wherein the second electric contact is arranged as a cylindrical ring made of electrically conductive material.

4. The laboratory sample distribution system according to claim 1, wherein a distance between the printed circuit board and the first electric contact is identical to a distance between a longitudinal end of the sleeve opposite to the printed circuit board and the second electric contact.

5. The laboratory sample distribution system according to claim 1, wherein the sleeves are detachably mounted on the printed circuit board.

6. The laboratory sample distribution system according to claim 1, wherein each sleeve comprises an electric isolation between an inner surface of the sleeve and the first electric contact and the second electric contact.

7. The laboratory sample distribution system according to claim 1, wherein the printed circuit board comprises a number of position sensors.

8. The laboratory sample distribution system according to claim 1, wherein the first coil electric contact is configured as a spring contact.

9. The laboratory sample distribution system according to claim 1, wherein the second coil electric contact is configured as a spring contact.

10. The laboratory sample distribution system according to claim 1, wherein a distance between a first longitudinal end of the coil and the first coil electric contact is identical to a distance between a second longitudinal end of the coil opposite to the first longitudinal end and the second coil electric contact.

11. The laboratory sample distribution system according to claim 1, further comprising,
a number of sample container carriers, each comprising at least one magnetically active device and adapted to move on the transport plane, and
a control unit configured to control the movement of the sample container carriers on the transport plane by driving the coils as electro-magnetic actuators such that the sample container carriers move along corresponding transport paths.

12. A laboratory automation system, the laboratory automation system comprising:
a number of laboratory stations; and
a laboratory sample distribution system according to claim 1 adapted to distribute the sample container carriers between the stations.

13. The laboratory automation system according to claim 12, wherein the number of laboratory stations comprise pre-analytical, analytical and/or a post-analytical stations.

* * * * *

UNITED STATES PATENT AND TRADEMARK OFFICE
CERTIFICATE OF CORRECTION

PATENT NO. : 9,939,455 B2  
APPLICATION NO. : 15/436051  
DATED : April 10, 2018  
INVENTOR(S) : Hans Schneider et al.

Page 1 of 1

It is certified that error appears in the above-identified patent and that said Letters Patent is hereby corrected as shown below:

On the Title Page

Item (30), Foreign Application Priority Data:  
Replace "14191456.6" with -- 14191455.6 --.

Signed and Sealed this  
Nineteenth Day of June, 2018

Andrei Iancu  
*Director of the United States Patent and Trademark Office*